US00PP33405P2

(12) United States Plant Patent
Austin

(10) Patent No.: US PP33,405 P2
(45) Date of Patent: Aug. 31, 2021

(54) SHRUB ROSE PLANT NAMED 'AUSRAVELOE'

(50) Latin Name: *Rosa hybrida*
Varietal Denomination: AUSraveloe

(71) Applicant: David Austin Roses Ltd., Wolverhampton (GB)

(72) Inventor: David J. C. Austin, Wolverhampton (GB)

(73) Assignee: David Austin Roses Ltd., Wolverhampton (GB)

( * ) Notice: Subject to any disclaimer, the term of this patent is extended or adjusted under 35 U.S.C. 154(b) by 0 days.

(21) Appl. No.: 16/974,281

(22) Filed: Dec. 16, 2020

(51) Int. Cl.
*A01H 5/02* (2018.01)
*A01H 6/74* (2018.01)

(52) U.S. Cl.
USPC ..... Plt./107

(58) Field of Classification Search
USPC ..... Plt./101, 102, 107
See application file for complete search history.

*Primary Examiner* — Susan McCormick Ewoldt
*Assistant Examiner* — Karen M Redden
(74) *Attorney, Agent, or Firm* — KPPB LLP

(57) ABSTRACT

A variety of rose plant of the shrub class, named 'AUSraveloe'. The 'AUSraveloe' is a variety of a very healthy medium sized rose shrub showing arching growth with glossy dark green foliage producing soft mid-pink color, with medium-large sized cupped blooms held on red stems, with a relaxed petal formation set around a button-eye, and having a medium-strong Old Rose fragrance with accents of lemon, banana and apricot.

1 Drawing Sheet

Classification: The present invention relates to a new *Rosa hybrida* shrub of the market class 'English Rose'.

Variety denomination: The new plant has the varietal denomination 'AUSraveloe'.

ORIGIN OF INVENTION

This invention relates to a new and distinct variety of shrub rose plant named 'AUSraveloe', which was originated from the cross-pollination of the two 'unnamed' and unpatented seedlings of *Rosa hybrida*.

BACKGROUND OF THE INVENTION

The primary objective of this breeding was to produce a very healthy medium sized rose shrub showing arching growth with glossy dark green foliage producing soft mid-pink color, with medium-large sized cupped blooms held on red stems, with a relaxed petal formation set around a button-eye, and having a medium-strong Old Rose fragrance with accents of lemon, banana and apricot.

SUMMARY OF THE INVENTION

Among the features which distinguish the new variety from others presently available and commercial rose cultivars known to the inventor is the following combination of characteristics: repeat flowering soft mid-pink blooms with medium-large sized cupped blooms, reddish colored flowering stems and dark colored foliage, and having a medium-strong Old Rose fragrance.

Asexual reproduction of the new variety by budding as performed in Albrighton, Britain shows that the foregoing and other distinguishing characteristics come true to form and are established and transmitted through succeeding asexual propagations. 'AUSraveloe' may be asexually propagated by budding. The budding successfully occurred on an unpatented plant/rootstock *Rosa dumetorum* 'Laxa' for the observed plants.

COMPARISON WITH PARENTS

The maternal and paternal parents of 'AUSraveloe' are two unnamed seedlings. The new rose may be distinguished from its seed parent, by the following combination of characteristics: the seed parent is paler in color and has larger, deeply cupped petals with fewer petals compared to the flowers of 'AUSraveloe'. The new rose may be distinguished from its pollen parent, by the following combination of characteristics: the pollen parent also has larger, deeply cupped flowers with a more apricot pink color, and is less disease resistant compared to 'AUSraveloe'.

COMPARISON WITH THE CLOSEST COMMERCIALLY AVAILABLE CULTIVAR

The closest commercially available cultivar to the new variety is 'AUSmixture' (U.S. Plant Pat. No. 27,365). While both blooms are predominantly pink in color 'AUSmixture' has a color of RHS 62B whereas 'AUSraveloe' is predominantly RHS 69A. 'AUSmixture' also has fewer petals when compared to 'AUSraveloe'. In addition, the flowering stems of 'AUSmixture' are predominantly green in color whereas the stems of 'AUSraveloe' are predominantly red in color. 'AUSmixture' also exhibits a fruity fragrance whereas 'AUSraveloe' has an Old Rose fragrance. Finally, 'AUSmixture' has fewer thorns when compared to 'AUSraveloe'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (2001) except where common terms of color definition are employed.

DESCRIPTION OF THE NEW VARIETY

Observations of budded 'AUSimage' specimens were made at a nursery in Albrighton, Wolverhampton, United Kingdom. The following description is of 2 year-old rose plants of the new variety grown in a garden environment in Albrighton, Britain in the month of July. Phenotypic expression may vary with environmental, cultural and climatic conditions, as well as differences in conditions of light and soil.

FLOWER CHARACTERISTICS

Blooming habit: Recurrent. The number of blooms per plant during the growing season is profuse, but there are too many to count.

Bud:

*Size*.—About 1.8 cm long and 1.6 cm in diameter when the petals start to unfurl.

*Form*.—The bud form is pointed ovoid.

*Color*.—When sepals first divide, the bud color is predominantly RHS 145B (yellow-green group) with flashes of RHS 186A (grayed-purple group) at the edges of the petals. When half blown, the upper sides of the petals are RHS 73B (red-purple group), and the lower sides of the petals RHS 73B (red-purple group).

*Calyx*.—Shape: star shape, with the sepals folding back against the stems. Length: 4.5 cm. Diameter: 4.5 cm.

*Sepals*.—Arrangement: Regularly arranged. Color: Upper Surface: RHS 139D (green group). Lower Surface: RHS 143C (green group) with RHS 184D (grayed-purple group). Length: 2 cm. Width: 0.9 cm. Shape: Lanceolate. Surface texture: Upper Surface: Hairy. Lower Surface: Downy. Number: There are 3 lightly appendaged sepals, and 2 unappendaged sepals with hairy edges.

*Receptacles*.—Color: RHS 143C (green group). Shape: Pitcher shaped. Size: Medium, about 1.0 cm long× 0.6 cm wide. Surface: Smooth.

*Peduncle*.—Length: Short, averaging about 5.5 cm. Surface: Smooth. Color: RHS 184B (grayed-purple group) with RHS 144B (yellow-green group) on the front side and RHS 144B (yellow-green group) on the reverse side. Strength: Strong.

Blooms:

*Size*.—Large, average open diameter is about 8.75 cm.

*Borne*.—Several together in clusters of 4-14 with blooms having a pyramidal shape.

*Stems*.—Strength: Strong, average length is about 4.5 cm. Diameter: 0.6 cm.

*Form*.—When first open, bloom is cupped. Permanence of bloom: outer petal edges curl back.

*Flower type*.—Double.

Petalage: Number of petals under normal conditions: approximately 100.

*Color*.—The upper sides of the petals are RHS 69D (red-purple group). The reverse sides of the petals are RHS 73B (red-purple group) on the top and RHS 73D (red-purple group) in the middle. The base of the petals has a medium sized basal spot that are RHS 3D (yellow group).

*Variegations*.—None.

*Discoloration*.—The general tonality at the end of the first day is RHS 69A (red-purple group), and at the end of the third day is RHS 69C (red-purple group).

*Fragrance*.—Moderate to strong. Character of fragrance: Old Rose.

Petals:

*Texture*.—Velvety.

*Size*.—Width: 1.7 cm.

*Length*.—3 cm.

*Surface*.—Smooth.

*Shape*.—Obovate.

*Margin*.—Mostly entire. Approximately 20% exhibit a central notch at the apex.

*Apex shape*.—Obtuse.

*Base shape*.—Rounded.

*Form*.—Incurved.

*Arrangement*.—Quartered.

*Petaloids*.—Number: 0-10. Color: RHS 69A (red-purple group). Length: 1-1.5 cm. Width: 0.5-1 cm. Shape: Obovate. Margin: Entire.

*Persistence*.—Petals drop off cleanly before drying.

*Lastingness*.—On the plant: Fair about 4-7 days. As a cut flower: not tested.

Reproductive parts:

*Stamens*.—Number: 10-15. Length: approximately 0.5 cm.

*Anthers*.—Length: approximately 0.15 cm. Color: RHS 13C (yellow group). Arrangement: Mixed with petaloids.

*Filaments*.—Color: RHS 12A (yellow group). Length: approximately 0.3-0.4 cm.

*Pollen*.—Color: RHS 3A (yellow group). Amount: Scarce.

*Pistils*.—Number: approximately 20-25. Length: approximately 0.7 cm.

*Styles*.—Color: RHS 151C (yellow-green group). Length: approximately 0.6 cm.

*Stigmas*.—Color: RHS 184C (grayed-purple group). Length: approximately 0.1 cm.

*Hips*.—NONE Observed.

PLANT CHARACTERISTICS

Plant form: Shrub.

Plant growth: Vigorous.

Age to maturity: 2 years.

Mature plant: Height: 110 cm. Width: 140 cm.

Rootstock: *Rosa dumetorum* 'Laxa' for the observed plants in the United Kingdom.

Foliage:

*Number*.—Leaflets on normal mid-stem leaves is: 5 with instances of 7 (including terminal leaflet).

*Size*.—Medium, about 15 cm long×10 cm wide.

*Quantity*.—Normal. Number of leaves per flowering stem is: approx. 5.

*Color*.—New foliage: Upper side: RHS 146A (yellow-green group) with flashes of RHS 60A (red-purple group) at the edge. Lower side: RHS 59A (red-purple group) with touches of RHS 143B (green group) on the veins. Old foliage: Upper side: RHS 137A (green group). Lower side: RHS 146A (yellow-green group).

Leaflets:

*Size*.—About 6 cm long×3.3 cm wide.

*Shape*.—Pointed oval.

*Base shape*.—Cordate.

*Apex shape*.—Acuminate.

*Texture*.—Leathery.

*Glossiness*.—Glossy.

*Edge*.—Serrated.

*Serrations*.—Double towards the center of the leaflet and single towards the base and apex.

*Petiole*.—Color: RHS 71A (red-purple group) on top side with RHS 146C (yellow-green group) on the underside. Length: 2-3 cm. Width: 0.2 cm. Surface Texture: Glandular.

*Petiole rachis*.—Color: RHS 59A (red-purple group) on the top side with RHS 146C (yellow-green group) on the underside. Underside: with prickles.

*Stipules*.—Length: 2.5 cm, serrated. Color: RHS 146A (yellow-green group) with a tint of RHS 61A (red-purple group) towards the petiole.

*Auricle*.—Shape: Lanceolate. Length: 0.6 cm Width: 0.2 cm. Color: RHS 146A (yellow-green group).

*Vein color*.—Central vein: RHS 64A (red-purple group). Other veins: RHS 137A (green group).

*Venation pattern*.—Reticulate.

Wood:

*New wood*.—Color: RHS 183A (grayed-purple group). Bark: Smooth.

*Old wood*.—Color: RHS 184A (grayed-purple group) on the top half of the wood, fading to RHS 145A (yellow-green group) towards the main stems. Bark: Smooth.

Branching habit:

*Number*.—Approximately 3 per main stem.

*Dimensions*.—Length: 60 cm Diameter: 0.8 cm.

Stems:

*Mature stem*.—Length: 90 cm. Diameter: 1 cm.

*Internode distance*.—5.5 cm. The above measurements are all variable, depending on growing conditions in a season.

*Stem pubescence present*.—No.

Prickles:

*Quantity*.—On main canes from base: Ordinary. Number per stem length: 6 per 10 cm. On laterals from main canes: Ordinary. Number per stem length: 6 per 10 cm.

*Form*.—Hooked downward and deep concave.

*Length*.—0.9 cm.

*Color when young*.—RHS 185B (grayed-purple group).

*Color when mature*.—Some RHS 178A (grayed-red group) with tips of RHS 22B (yellow-orange group) and retaining some RHS 185B (grayed-purple group) throughout.

Small prickles:

*Quantity*.—Main stalk: Few. Number per stem length 5-8 per 10 cm. Laterals: Few. Number per stem length: 5-8 per 10 cm.

*Color*.—When young: RHS 185B (grayed-purple group). When mature: RHS 185B (grayed-purple group).

Disease resistance:

*Powdery mildew* (*podosphaera pannosa*).—Resistant.

*Downy mildew* (*peronospora species*).—Resistant.

*Blackspot* (*diplocarpon rosae*).—Resistant.

*Rust* (*phragmidium tuberculatum*).—Resistant.

Pest resistance: Not tested.

Winter hardiness: Not tested.

Growing conditions: Normal garden conditions.

What is claimed is:

1. A new and distinct variety of shrub rose plant named 'AUSRAVELOE', substantially as illustrated and described herein.

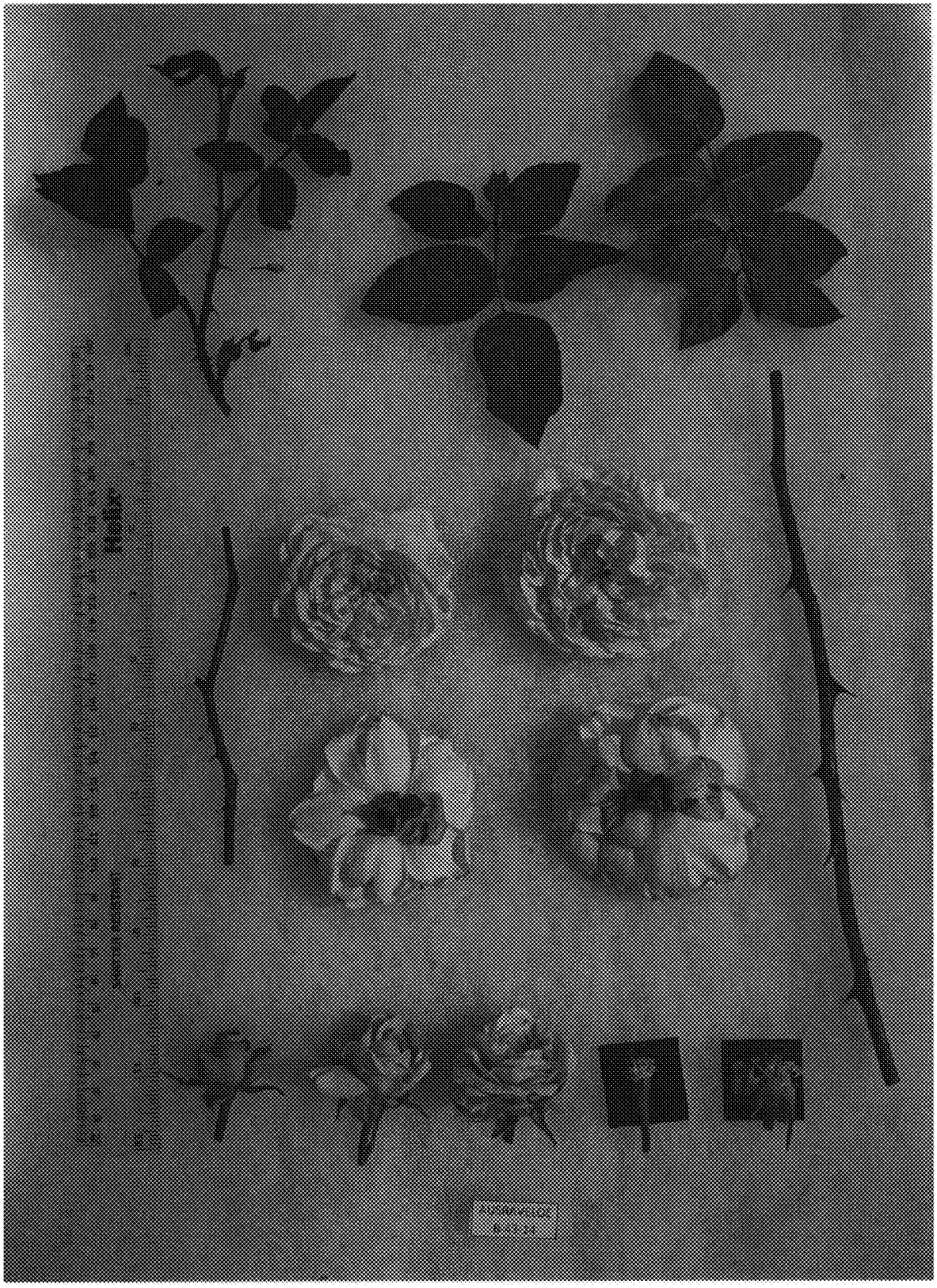

* * * * *